US006184990B1

(12) United States Patent
Amirkhanian et al.

(10) Patent No.: US 6,184,990 B1
(45) Date of Patent: Feb. 6, 2001

(54) MINIATURE MULTIPLE WAVELENGTH EXCITATION AND EMISSION OPTICAL SYSTEM AND METHOD FOR LASER-INDUCED FLUORESCENCE DETECTORS IN CAPILLARY ELECTROPHORESIS

(75) Inventors: Varouj Amirkhanian, Glendale; Sunil S. Deliwala, Placentia; Ronald W. Franck, Garden Grove; Bart J. Wanders, Trabuco Canyon; Gary Tepermeister, Laguna Niguel, all of CA (US)

(73) Assignee: Beckman Coulter, Inc., Fullerton, CA (US)

( * ) Notice: Under 35 U.S.C. 154(b), the term of this patent shall be extended for 0 days.

(21) Appl. No.: 09/470,894

(22) Filed: Dec. 22, 1999

(51) Int. Cl.[7] ................................................. G01N 21/00
(52) U.S. Cl. ...................... 356/440; 356/441; 356/410; 250/574
(58) Field of Search ..................... 356/440, 442, 356/441, 343, 246, 410, 336, 337, 338, 339; 250/574, 575; 422/82.08, 82.09, 82.05; 204/480.1; 362/32, 302, 346; 385/33, 119

(56) References Cited

U.S. PATENT DOCUMENTS

| | | | |
|---|---|---|---|
| 5,037,199 | * | 8/1991 | Hlousek ............................ 356/246 |
| 5,089,714 | * | 2/1992 | Ludlow et al. ..................... 250/574 |
| 5,484,571 | * | 1/1996 | Pentoney, Jr. et al. ........... 422/82.08 |
| 5,491,765 | * | 2/1996 | Matsumoto ........................ 385/33 |
| 5,584,557 | * | 12/1996 | Alexay ............................... 362/32 |

* cited by examiner

Primary Examiner—Frank G. Font
Assistant Examiner—Sang H. Nguyen
(74) Attorney, Agent, or Firm—William H. May; Margaret A. Kivinski

(57) ABSTRACT

An optical apparatus for and method of improving collection efficiency and signal strength of optical instruments used in capillary electrophoresis, such as laser-induced fluorescence detectors are provided. The apparatus and method provides a concave reflector positioned at one side of the capillary flow cell as a first high numerical aperture (N.A.) collector, a lens collector positioned at an opposite side of the flow cell as a second high N.A. collector, and an optical fiber positioned at close proximity of the flow cell for delivery of an excitation light to cause a sample contained in the flow cell to emit emission lights. The reflector has a concave surface for reflecting the emission lights, and the collector has a proximal convex surface for collecting the emission lights, and a distal convex surface for collimating the emission lights. This arrangement achieves a larger solid collection angle from both sides of the flow cell and therefore an increased collection efficiency. Two or more optical fibers may be used to deliver excitation lights from different sources. The optical fibers are arranged in a plane orthogonal to the optical axis of the reflector and collector to reduce the interference from the scattered background lights and therefore improve the signal to noise ratio. The collimated emission lights can be detected by, e.g., a photo-multiplier tube detector.

30 Claims, 7 Drawing Sheets

MINIATURE MULTIPLE WAVELENGTH EXCITATION AND EMISSION OPTICAL SYSTEM AND METHOD FOR LASER-INDUCED FLUORESCENCE DETECTORS IN CAPILLARY ELECTROPHORESIS

BACKGROUND OF THE INVENTION

1. Area of the Art

The present invention relates generally to the technology and device for fluorescence detection and more specifically to optical systems for laser-induced fluorescence detection in capillary electrophoresis, and methods of use thereof.

2. Description of the Prior Art

In fluorescence detection devices and technologies, it is important to improve the sensitivity of the fluorescence detectors. One of the key factors in improving the sensitivity of the fluorescence detectors is to collect maximum fluorescing radiation, i.e., providing the largest solid angle for collecting re-emitted fluorescence light from a flow cell containing moving analyte (i.e., CE and HPLC, etc.), while minimizing the background (i.e., collected excitation light intensity).

Therefore, in order to obtain optimum detection limit in a fluorescence detector, the fluorescence generated from the illuminated sample stream must be collected with high efficiency, while scattered excitation light reaching the detector must be minimized. In practice, high numerical aperture objectives or reflectors may be used to collect fluorescence. The fraction of light collected by a lens is related to the numerical aperture (N.A.) of the lens, and refractive index (n) of the surrounding medium. The following equation expresses this relationship:

$$\text{Collection Efficiency} = \text{Sin}^2(Arc\ \text{Sin}(N.A./n)/2) \quad [1]$$

where collection efficiency of 1 implies that the lens collects all of the light emitted by the sample.

Usually the light collecting lens is surrounded by air, which has a refractive index of 1 (n=1). From Equation [1], it can be seen that a lens of very high numerical aperture is required to obtain a high collection efficiency. A lens with a numerical aperture of 1 will collect 50% of the light emitted by the sample. Although lenses immersed in a liquid medium (oil, water, etc.) can have a numerical aperture (N.A.) greater than 1, they collect less than 50% of the emitted light because the refractive index of the immersion fluid is usually larger than the refractive index of the lens material. In addition, according to Equation [1], a lens with a numerical aperture of 0.5 and immersed in air collects only 7% of the emitted light.

In conventional art, refractive and/or reflective optical collectors are utilized in laserinduced fluorescence (LIF) detectors with or without optical fibers for collecting the emitted fluorescing radiation. However, the capability of these collectors to collect fluorescence light is limited by their maximum collection angle. A typical high collector will have a collection cone angle of about 90 degrees. This corresponds to a 0.7 N.A., or 14% collection efficiency, (according to Equation [1]) in the optical system for a fluorescence based detector.

One example of a conventional 6–7% collection efficiency optical system is an LIF detector disclosed by U.S. Pat. No. 5,614,726 issued to Kaye et al. on Mar. 25, 1997 for "Automated Optical Alignment System and Method Using Raman Scattering of Capillary Tube Contents." The fluorescence detector disclosed by Kaye uses a single excitation fiber which is the means for delivering the excitation light from the laser source to the capillary. As laser light is launched into a section of the capillary, due to the tubular nature of fused silica capillary, an isotropic (i.e., equally in all direction) excitation light scattering in the same plane as the incident light is produced. The fluorescence is collected by an ellipsoidal mirror and focused on to a photo-multiplier tube (PMT) detector. A collection mirror (i.e., the ellipsoidal reflector) with a through hole at the center is located in the opposite side and on the same plane as the excitation fiber which allows most of the unwanted excitation light from the fiber to pass into an empty dump hole. This dump hole is large enough to allow the passage of the excitation fiber's light cone, which is about 25 degrees (N.A.=0.22) for this case. The scattered (unwanted) excitation light is further attenuated by a beam block. With all these baffles and beam dumps, the collection efficiency capability of this system is about 6–7% (0.7 N.A. for the mirror minus 0.2 N.A. is equal to 0.5 N.A. or approximately 7% collection efficiency).

Therefore, a need exists to develop a new LIF detector in capillary electrophoresis that has a higher collection efficiency optics and enhanced signal strength.

SUMMARY OF THE INVENTION

It is an object of the present invention to improve the collection efficiency and emission signal strength of laser-induced fluorescence detectors in capillary electrophoresis.

It is also an object of the present invention to provide a novel miniature multiple wavelength excitation and emission optical system for laser-induced fluorescence detectors in capillary electrophoresis.

These and other objects and advantages are achieved in a miniature multiple wavelength excitation and emission optical system for laser-induced fluorescence detectors in capillary electrophoresis. The system of the present invention comprises a first spherical reflector and collector on one side of the capillary flow cell, and a second sapphire ball (or modified lens) collector and collimator on the opposite side of the flow cell, where excitation light from multiple sources are delivered by optical fibers arranged in the plane orthogonal to the axis of the collection optics.

Such an arrangement has been found to provide a number of advantages. As explained in greater detail below, it has been found that by providing a first spherical reflector and collector on one side of the capillary flow cell, and a second ball (or modified) lens collector and collimator on the opposite side of the flow cell, a larger solid collection angle can be obtained from each side of the flow cell, which results in increased collection efficiency and enhanced signal strength. It has also been found that by arranging the optical fibers which deliver the excitation lights in the plane orthogonal to the axis of the collection optics, the leakage of back-scattered excitation light to the collection optics is reduced, which results in a lower scattered background and a higher signal-to-noise fluorescence detection. Furthermore, the design is self aligning with respect to the flow cell, without any moving optical parts.

The present invention is well suited for use in detection of fluorescence in a capillary flow cell of a capillary zone electrophoresis instrument such as, but not limited to, the P/ACE MDQ™ Capillary Electrophoresis System, available from Beckman Coulter, Inc. It can also be applied to multiple capillary fluorescence detectors. The arrangement of the present invention can easily accommodate multiple excitation wavelengths to excite multiple fluorescence species in a sample. Furthermore, it can be readily coupled to a filter based or dispersive spectrophotometer (FIG. 9) instrument for performing analysis of the spectral information to quantify the amount of fluorescing species in a given sample in the flow cell.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

The present invention provides a miniature multiple wavelength excitation and emission optical system for laser-induced fluorescence detectors in capillary electrophoresis.

Figure 1:
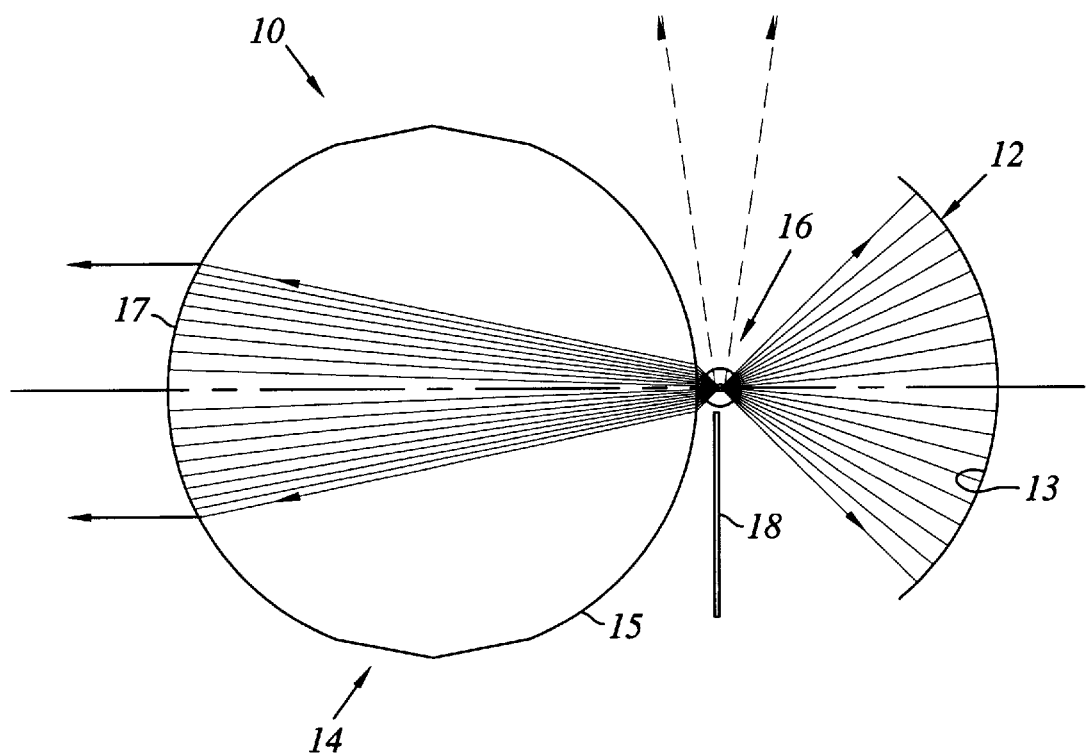
FIG. 1 is an illustrative diagram showing a preferred embodiment of the miniature multiple wavelength excitation and emission optical system of the present invention for laser-induced fluorescence detectors in capillary electrophoresis, the system providing a spherical reflector as a high numerical aperture (N.A.) collector on one side of the capillary flow cell, and a high refractive index sapphire ball lens as a second high N.A. collector and collimator on the opposite side of the flow cell.

Referring to FIG. 1, there is an illustrative diagram showing a preferred embodiment of the miniature multiple wavelength excitation and emission optical system of the present invention for laser-induced fluorescence detectors. The optical system 10 utilizes a concave reflector 12 as a high numerical aperture (N.A.) collector, and a high refractive index lens 14 as a second high N.A. collector and collimator. Reflector 12 is positioned on one side of a capillary flow cell 16, and collector 14 is positioned on the opposite side of the flow cell 16. For the purpose of the present invention, the flow cell may be a capillary flow cell used in capillary electrophoresis or a flow cell used in HPLC technique. Reflector 12 has a spherical concave surface 13 for reflecting the emission lights. Collector 14 has a first spherical convex surface 15, which is proximal to the flow cell 16, for collecting the emission lights, and a second spherical convex surface 17, which is distal to the flow cell 16, for collimating the emission lights. As an example, in optical system 10, the radius of the spherical concave surface 13 of reflector 12 may be 3 millimeters (mm). The collector may be a sapphire ball lens where the first and second spherical convex surfaces 15 and 17 are two portions of the spherical surface of the ball lens, and the radius of the ball lens may be 2.5 mm. It should be understood that the radius of the reflector 12 or ball lens of the collector may vary depending on the size of the flow cell, and are readily determined by one skilled in the art in view of the disclosure of the present invention.

The optical system of the present invention may also include an optical fiber 18 for delivery of the excitation light. Optical fiber 18 may be positioned in close proximity of the flow cell 16 for delivering the excitation light. After the delivery of the excitation light by optical fiber 18, the emission lights are reflected by reflector 12, then collected and collimated by collector 14 for subsequent fluorescence detection.

The arrangement of optical system 10 achieves a higher solid angle of larger than 0.8 N.A. for collection of the emission lights from each side of the flow cell 16, and a total collection efficiency of more than 40% (20% from each side of the flow cell), according to Equation [1]. This enhances the signal strength by at least a factor of 5.

Figure 2:
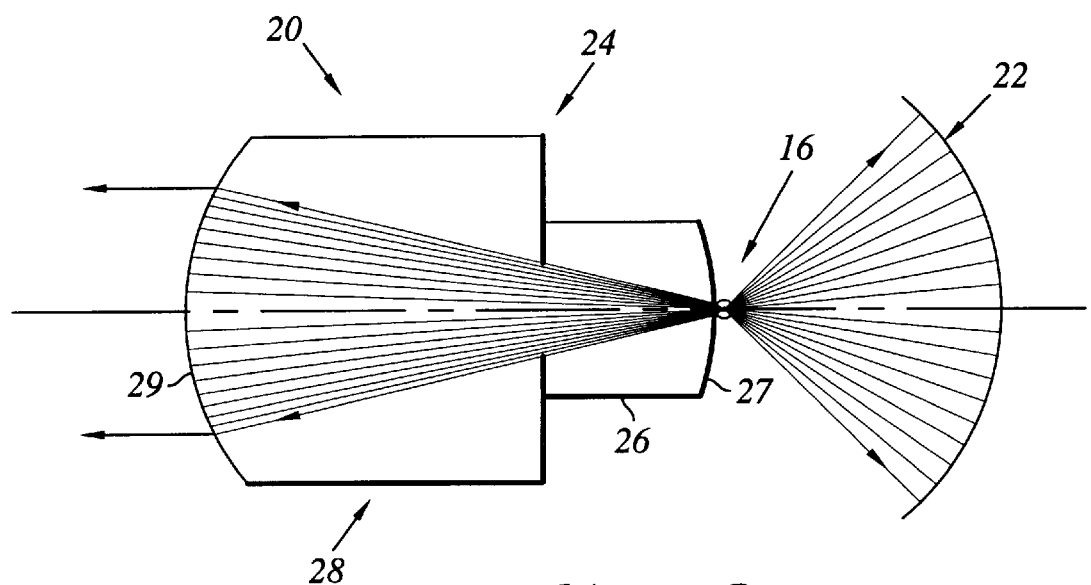
FIG. 2 is an illustrative diagram showing another preferred embodiment of the optical system of the present invention, utilizing a spherical reflector as a high numerical aperture (N.A.) collector on one side of the capillary flow cell, and a modified high refractive index sapphire lens as a second high N.A. collector and collimator on the opposite side of the flow cell.

Referring to FIG. 2, there is an illustrative diagram showing another preferred embodiment of the present invention of the miniature multiple wavelength excitation and emission optical system for laser-induced fluorescence detectors in capillary electrophoresis. The optical system 20 also utilizes a spherical reflector 22 as a high numerical aperture (N.A.) collector positioned on one side of the capillary flow cell 16. However, on the opposite side of the flow cell 16, there is positioned a modified high refractive index sapphire lens 24 as a second high N.A. collector and collimator. The modified collector lens 24 has two spherical surfaces 26 and 28. Smaller diameter side 26 has a spherical surface 27 facing the flow cell 16, and larger diameter side 28 has a spherical surface 29. The two spherical surfaces 27 and 29 are respective portions of an overall spherical ball surface similar to that of the ball lens 14 in FIG. 1. As an example, the radius of spherical surface 27 may be 2.5 mm, and the radius of spherical surface 29 may be 2.5 mm. The optical effect of the modified lens 24 is the same as that of the ball lens 14 in FIG. 1. Nonetheless, the lens 14 can be less expensive yet easier to manufacture and handle.

Figure 3:
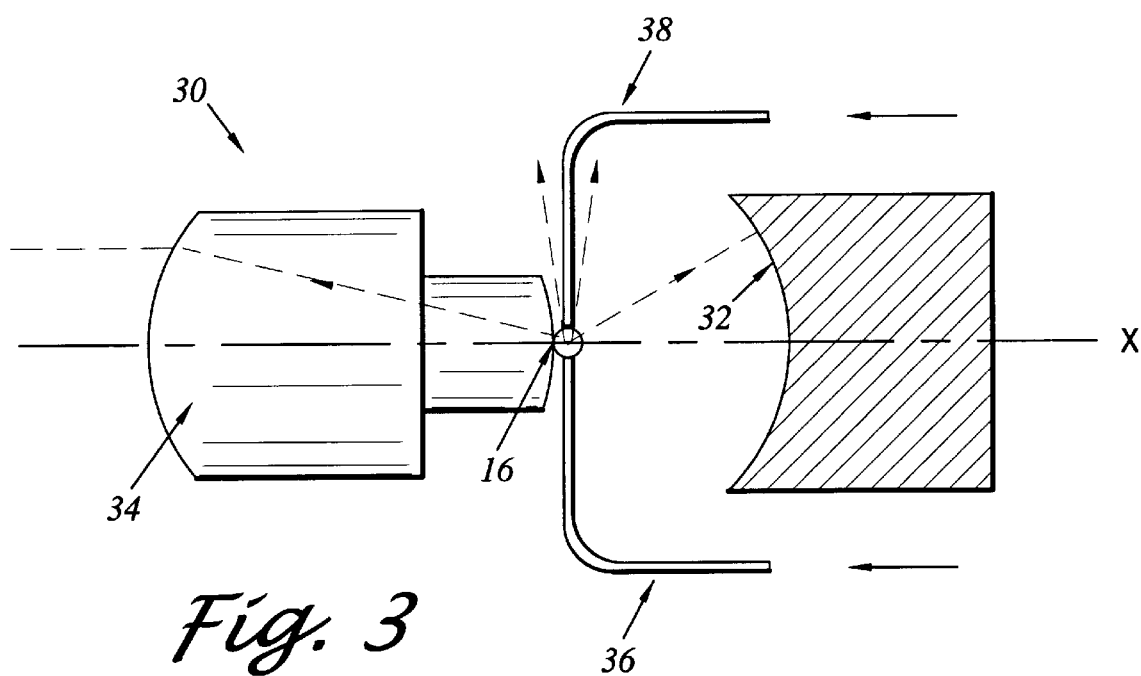
FIG. 3 is an illustrative diagram showing still another preferred embodiment of the optical system of the present invention, utilizing two optical fibers for delivery of the excitation light from multiple light sources.

Referring to FIG. 3, there is an illustrative diagram showing still another preferred embodiment of the present invention of the miniature multiple wavelength excitation and emission optical system for laser-induced fluorescence detectors in capillary electrophoresis. Similar to the optical arrangement shown in FIG. 2, the optical system 30 utilizes a spherical reflector 32 as a high numerical aperture (N.A.) collector positioned on one side of the capillary flow cell 16, and a modified high refractive index sapphire lens 34 as a second high N.A. collector and collimator positioned on the opposite side of the flow cell 16. However, in this system 30, two optical fibers 36 and 38 are utilized for delivery of the excitation lights from two or more different sources. As an example, one optical fiber 36 may be used to deliver a first excitation laser light of 635 nanometer (nm) wavelength, and the other optical fiber 38 may be used to deliver a second excitation laser light of 488 nm wavelength. This arrangement enables multiple fluorescence species in the same sample to be excited at the same time for simultaneous detection.

Figure 4:
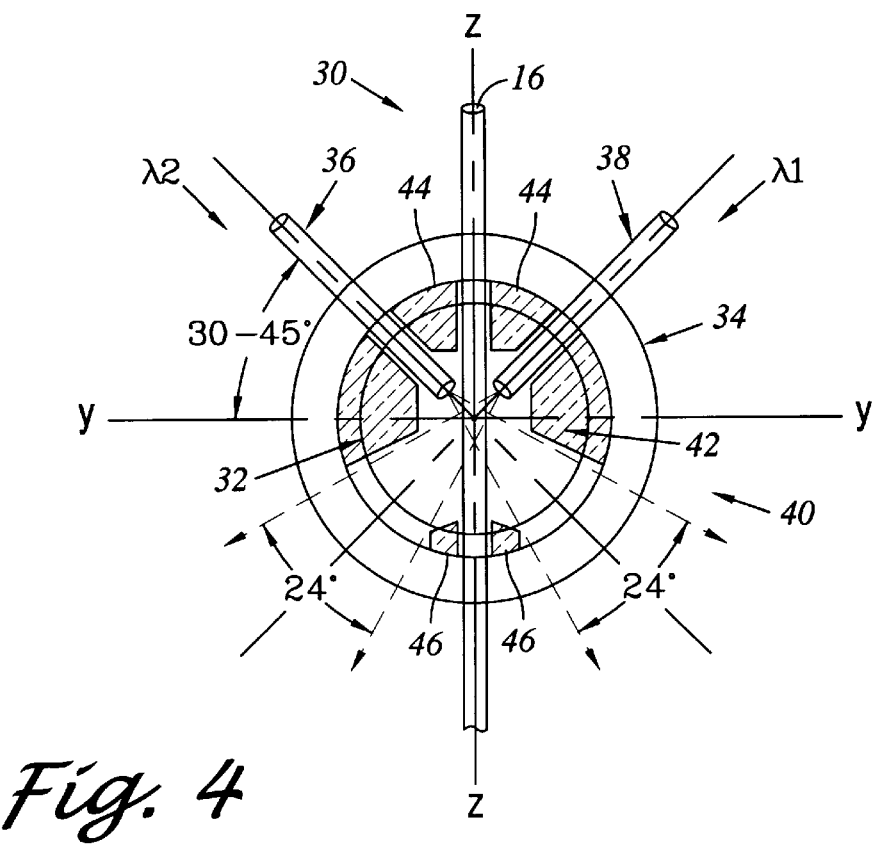
FIG. 4 is an illustrative diagram showing the two optical fibers of the optical system of the present invention delivering the excitation lights in the plane orthogonal to the axis of the collection optics.

Referring to FIG. 4, there is an illustrative diagram showing a preferred optical arrangement of the optical system 30 shown in FIG. 3. In this arrangement, a fiber and capillary alignment assembly 40 is provided between the reflector 32 and collector 34. Assembly 40 has component portions 42, 44 and 46 as shown in their cross-sectional configurations. Capillary flow cell 16 is aligned along the vertical Z-axis and extending through the opening between component portions 44 and the opening between component portions 46 of assembly 40. Excitation light delivery fibers 36 and 38 are diagonally aligned and extended through a V-shaped channel formed by the openings between respective component portions 44 and 42. Therefore, the optical fibers 36 and 38 are in the Y-Z plane orthogonal to the common axis of the collection optics (i.e., the X-axis which is perpendicular to the Y-Z plane). As an example, the angle between fiber 36 or 38 and the Y-axis may be 30 to 45 degrees. Further, the openings between respective component portions 44 and 42 may form a V-shaped "beam dump" for allowing the scattered excitation lights to escape. As an example, each opening of the V-shaped "beam dump" may be approximately 24°.

In this arrangement, since the excitation fibers are in a plane orthogonal to the axis of the collection optics and are at a close proximity of the flow cell, the leakage of the scattered background lights is attenuated, which, combined with the improved collection efficiency, results in a higher signal-to-noise ratio fluorescence detection system.

Figure 5:
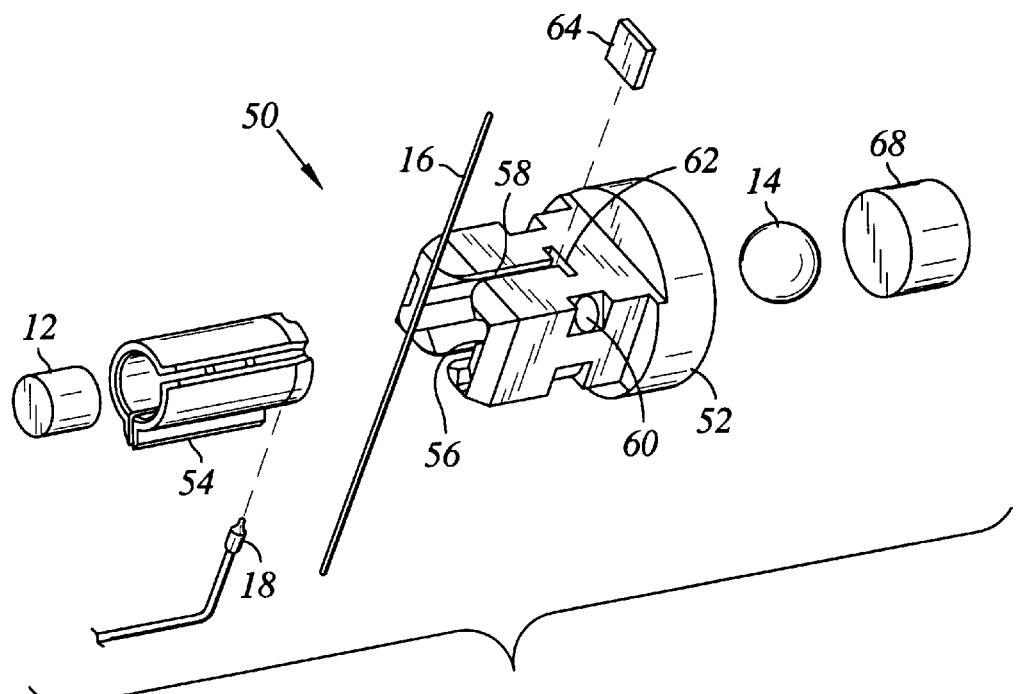
FIG. 5 is an exploded diagram showing a plug and probe assembly utilized in one of the preferred embodiments of the miniature multiple wavelength excitation and emission optical system of the present invention for laser-induced fluorescence detectors.
Figure 6:
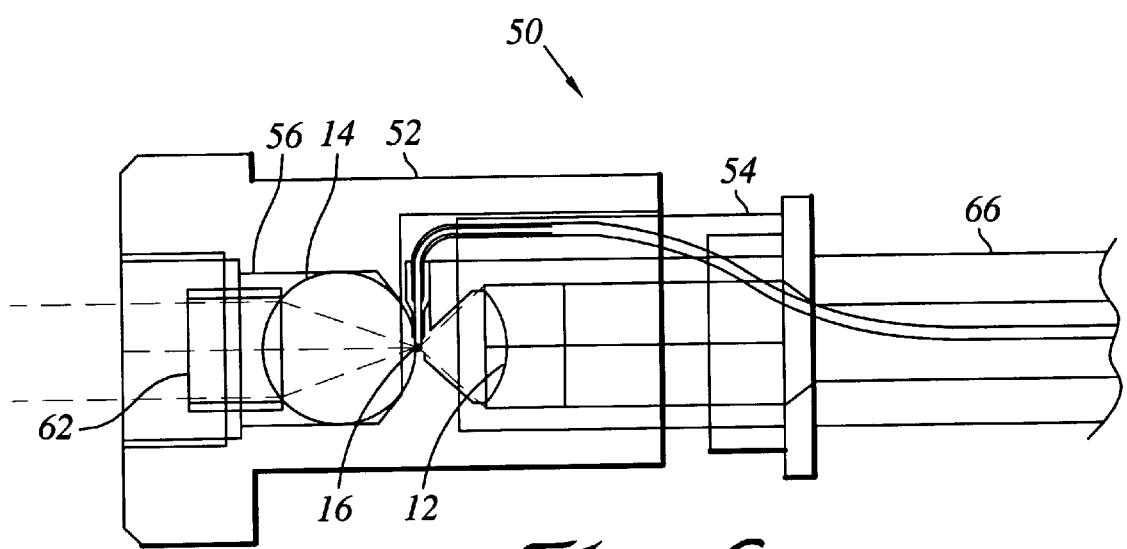
FIG. 6 is an illustrative diagram showing the plug and probe assembly as assembled.

Referring to FIGS. 5 and 6, there is shown a plug and probe assembly 50 utilized in the present invention optical system. The plug and probe assembly 50 includes a plug member 52 and a probe member 54 which are slidably engageable and can be assembled together to hold and align the spherical reflector 12 and the sapphire ball lens collector 14 on the two opposite sides of the flow cell 16. The plug member 52 has an internal bore 56 for housing the collector 14 and reflector 12 for insertion of the probe member 54. The plug member 52 also has external slots 58 for passing through the capillary flow cell 16. The plug member 52 may further have opening(s) 60 for allowing the scattered background emission lights to escape, and a slot 62 for insertion of a pad 64. The plug and probe assembly 50 also includes a probe stem 66 for guiding the excitation light delivery fiber 18, and a plug holder 68 for holding the sapphire ball lens 14. The plug and probe assembly 50 can easily accommodate multiple optical fibers for delivery of excitation laser light from different sources to excite multiple fluorescent species in the sample contained in the flow cell.

Figure 7:
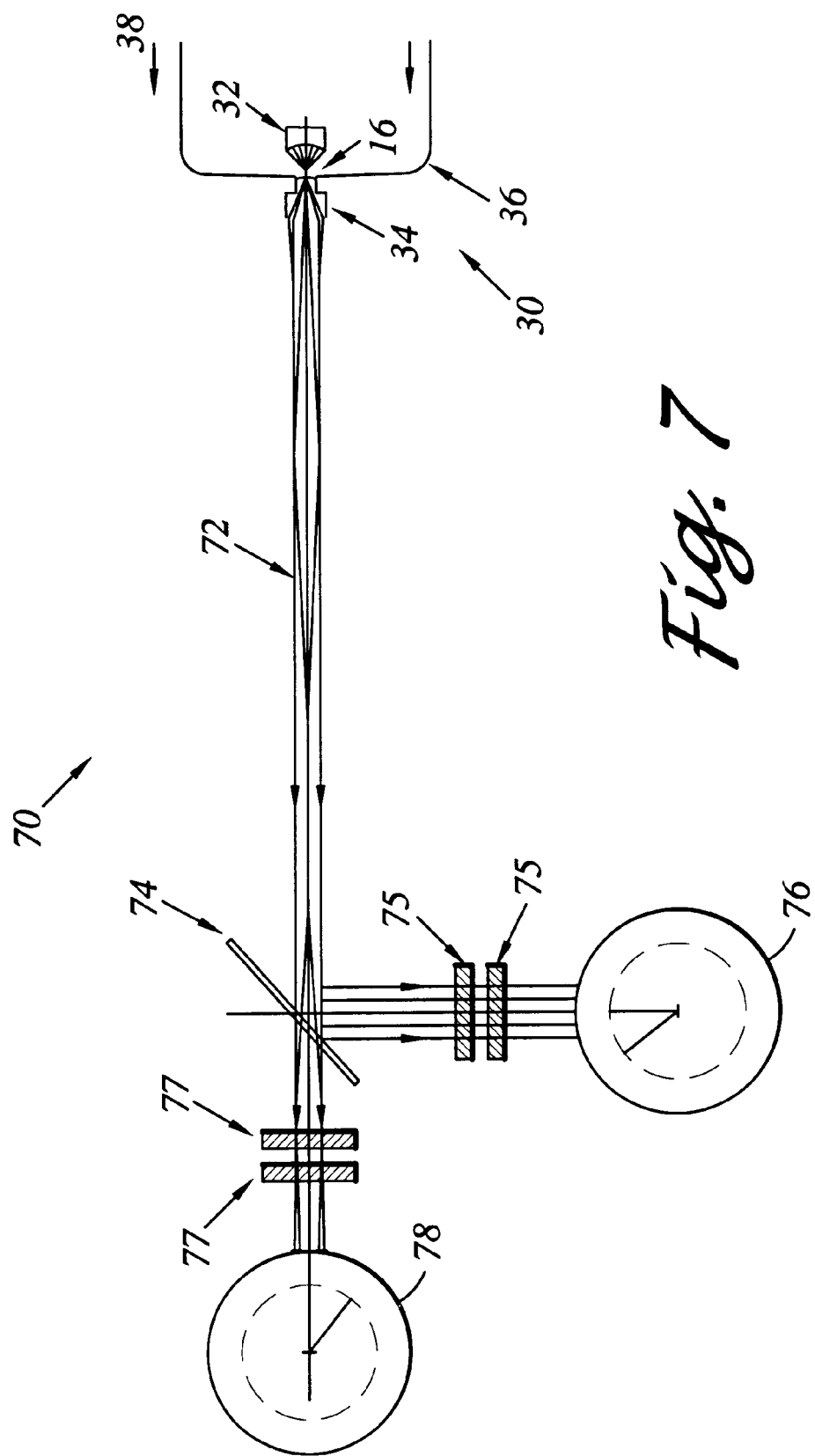
FIG. 7 is an illustrative diagram showing a laser-induced fluorescence capillary zone electrophoresis detection instrument incorporating the miniature multiple wavelength excitation and emission optical system of the present invention.

Referring to FIG. 7, there is an illustrative diagram showing a laser-induced fluorescence (LIF) capillary zone electrophoresis detection instrument 70 incorporating the miniature multiple wavelength excitation and emission optical system 30 of the present invention. The LIF detection instrument 70 incorporates the optical system 30 as described above, which includes a spherical reflector 32 and a modified spherical collector 34 positioned on the two opposite sides of the capillary flow cell 16 respectively. Two optical fibers 36 and 38 are used for delivery of the excitation lights from two different laser sources. The emission lights from the sample contained in the capillary flow cell 16 are reflected by reflector 32, and collected and collimated by collector 34 as a collimated beam 72. The LIF detection instrument 70 also incorporates a beam splitter 74, a first set of emission filters 75, a first photo-multiplier tube (PMT) detector 76, a second set of emission filters 77, and a second PMT detector 78. As an example, the beam splitter may be a 50/50 splitter. The two PMT detectors 76 and 78 can be used to detect the fluorescence emissions from the capillary flow cell excited by the laser lights of two different wavelengths delivered by the two optical fibers respectively.

Figure 8:
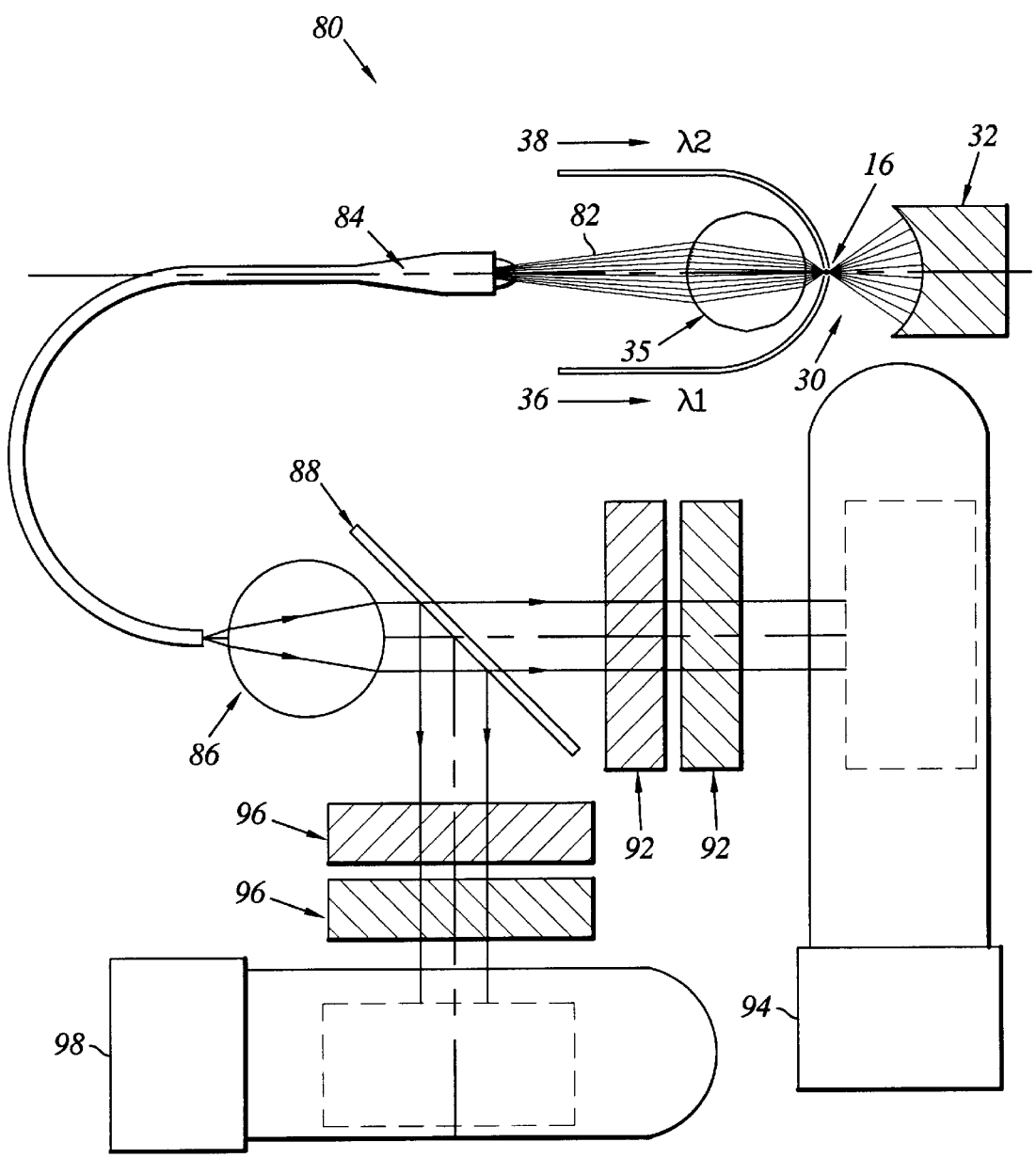
FIG. 8 is an illustrative diagram showing a filter based or dispersive spectrophotometer instrument incorporating the miniature multiple wavelength excitation and emission optical system of the present invention.
Figure 9:
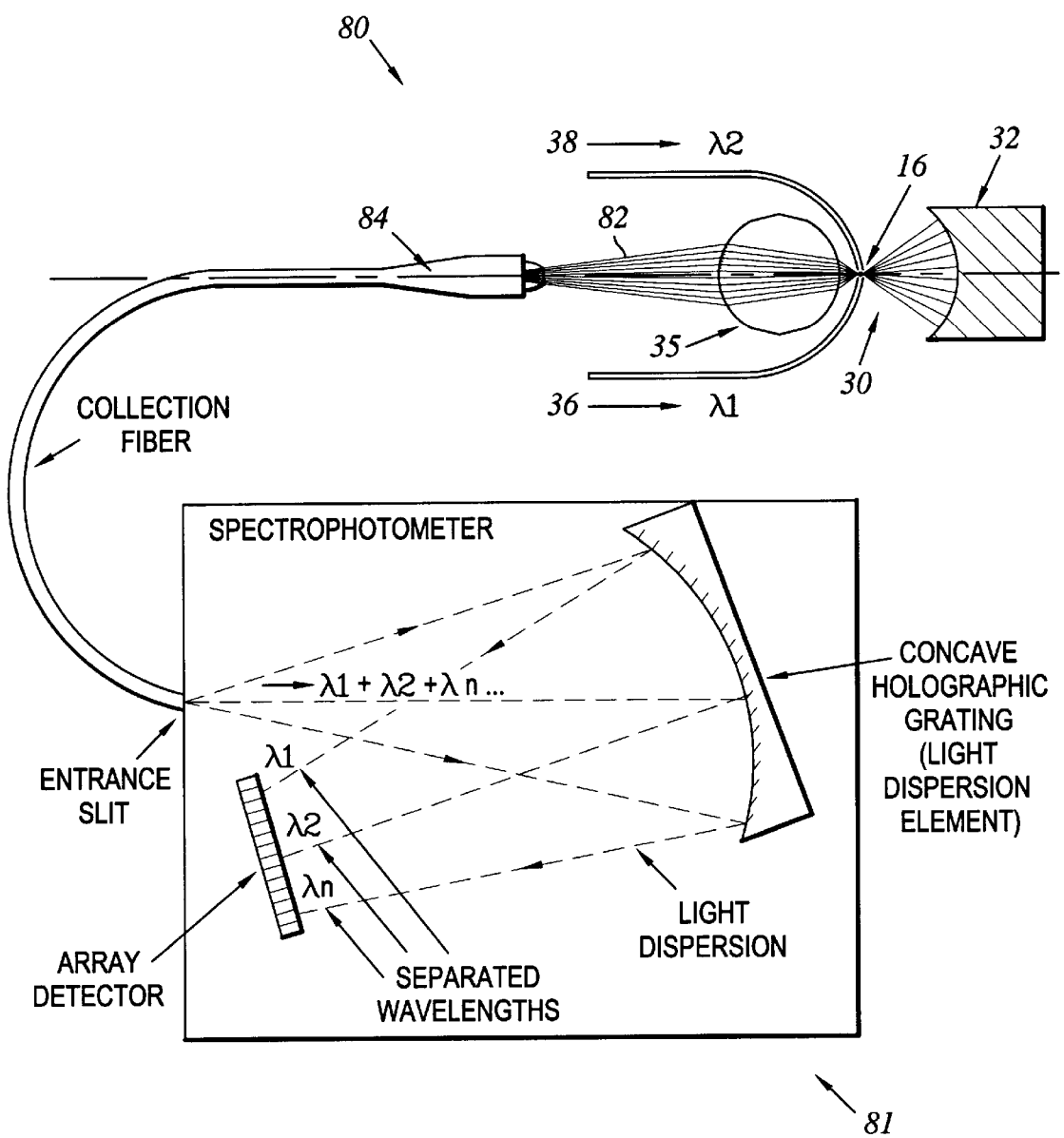
FIG. 9 is an illustrative diagram showing a preferred embodiment of the present invention coupled to a dispersive spectrophotometer instrument.

Referring to FIG. 8 and FIG. 9, there are illustrative diagrams showing that the optical system of the present invention can be easily incorporated into a filter based 80 or dispersive spectrophotometer instrument 81. The spectrophotometer instrument 81 incorporates an optical system 30 as described above, which includes a spherical reflector 32 and a sapphire ball lens collector 35 positioned on the two opposite sides of the capillary flow cell 16, respectively. Two optical fibers 36 and 38 are used for delivery of the excitation lights from two different laser sources. The emission lights from the sample contained in the capillary flow cell 16 are reflected by reflector 32, and collected and refocused by collector 35. The refocused beam 82 is delivered by an optical fiber 84 to a lens 86 and then split by a beam splitter 88. As an example, the beam splitter may be a 45° inclined 50/50 splitter. The spectrophotometer further incorporates a first set of emission filters 92, a first PMT detector 94, a second set of emission filters 96, and a second PMT detector 98. The emission light output from fiber 84 could also be spectrally analysed by a grating base monochromator setting device using an array detector (FIG. 9). This arrangement can be used for performing analysis of the spectral information to quantify the amount of different fluorescing species in a given sample in the capillary flow cell.

Figure 10:
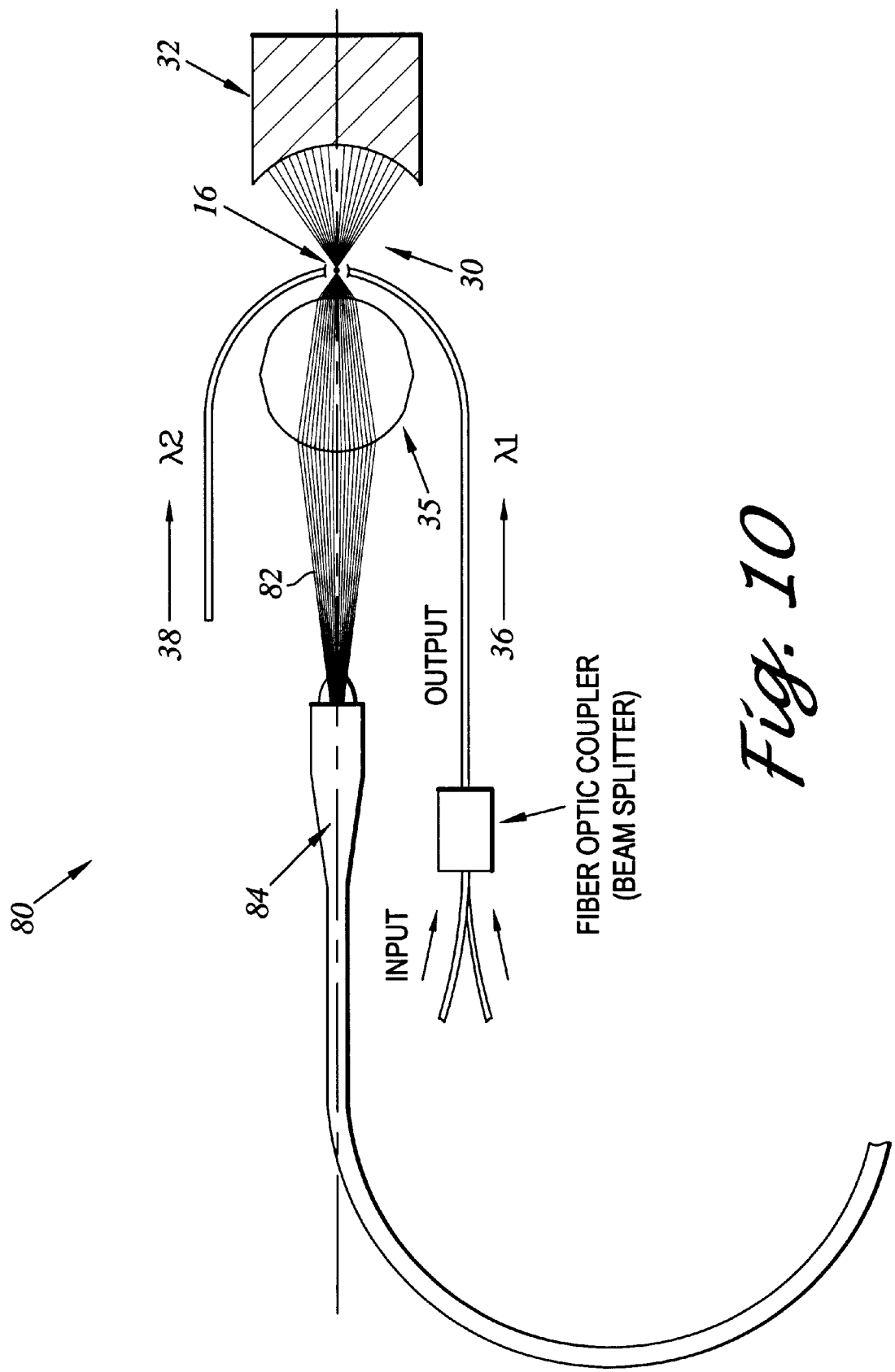
FIG. 10 is an illustrative diagram showing another preferred embodiment of the present invention in which more than two wavelengths are excitation light sources.

FIG. 10 is an illustrative drawing showing the possibility of having more than two wavelengths as excitation light sources using fiber optic couplers or beam combiners. These beam combiners could have several (more than one) fibers at the input end and one fiber at the output end, before the capillary. The present invention is therefore not limited to two wavelength excitation and emission. The capability for multiwavelength excitation and emission is contemplated.

The present invention also provides a method of improving collection efficiency in an optical instrument for capillary electrophoresis utilizing a capillary flow cell. The essential steps of the method include delivering an excitation light at a close proximity of the flow cell to cause the sample to emit emission lights, positioning a concave reflector having a concave surface at one side of the flow cell such that the concave surface reflects the emission lights, positioning a lens collector having a proximal convex surface and a distal convex surface at an opposite side of the flow cell such that the proximal convex surface collects the emission lights and the distal convex surface collimates the emission lights, and detecting the collimated emission lights.

The present invention method may include the step of forming the collector with a high refractive index ball lens, or with a first lens having the proximal convex surface and a second lens having the distal convex surface. It may also include the step of delivering the excitation light along a direction in a plane orthogonal to a common optical axis of the reflector and the collector.

The present invention method may further include the step of delivering several (more than one) additional excitation light at a close proximity of the flow cell to cause the sample to emit additional emission lights. The excitation light may be delivered along respective diagonal directions in a plane orthogonal to a common optical axis of the reflector and the collector.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. An optical apparatus to be used in conjunction with an optical instrument for optical detection, utilizing a capillary flow cell containing a sample, the optical apparatus comprising:
    a. a concave reflector with an optical axis positioned at one side of said flow cell;
    b. a lens collector positioned at an opposite side of said flow cell;
    c. means positioned at close proximity of said flow cell for delivery of an excitation light along a direction in a plane orthogonal to said optical axis to cause said sample to emit emission lights;
    wherein said reflector having a concave surface for reflecting said emission lights; and said collector having a proximal convex surface for collecting said emission lights, and a distal convex surface for collimating said emission lights.

2. The optical apparatus as defined in claim 1, wherein said collector is a high refractive index ball lens.

3. The optical apparatus as defined in claim 1, wherein said collector further comprises a first lens having said proximal convex surface and a second lens having said distal convex surface.

4. The optical apparatus as defined in claim 1, wherein said excitation light delivery means comprises an optical fiber.

5. The optical apparatus as defined in claim 1, wherein said excitation light delivery means is located in said plane.

6. The optical apparatus as defined in claim 1, further comprising at least one additional means positioned at close proximity of said flow cell for delivery of another excitation light to cause said sample to emit additional emission lights.

7. The optical apparatus as defined in claim 6, wherein said at least one additional excitation light delivery means further comprises an optical fiber.

8. The optical apparatus as defined in claim 6, wherein said excitation light delivery means and said at least one additional excitation light delivery means are located in said plane.

9. The optical apparatus as defined in claim 6, wherein said excitation light delivery means and said at least one additional excitation light delivery means are diagonally aligned in said plane.

10. The optical apparatus as defined in claim 1, further comprising a plug and probe assembly for holding said reflector and said collector and aligning said flow cell and said excitation light delivery means.

11. The optical apparatus as defined in claim 1, wherein said concave surface of said reflector is spherical and continuous.

12. An optical system for optical detection utilizing a capillary flow cell containing a sample, the optical instrument comprising:
    a. an optical apparatus comprising a concave reflector with an optical axis positioned at one side of said flow cell, a lens collector positioned at an opposite side of said flow cell, and means positioned at close proximity of said flow cell for delivery of an excitation light along a direction in a plane orthogonal to said optical axis to cause said sample to emit emission lights;
        wherein said reflector having a concave surface for reflecting said emission lights; and
        said collector having a proximal convex surface for collecting said emission lights, and a distal convex surface for collimating said emission lights; and
    b. means for detection of said collimated emission lights.

13. The optical system as defined in claim 12, wherein said collector of said optical apparatus is a ball lens.

14. The optical system as defined in claim 12, wherein said collector of said optical apparatus further comprises a first lens having said proximal convex surface and a second lens having said distal convex surface.

15. The optical system as defined in claim 12, wherein said excitation light delivery means of said optical apparatus is located in said plane.

16. The optical system as defined in claim 12, wherein said optical apparatus further comprises at least one additional means positioned at close proximity of said flow cell for delivery of another excitation light to cause said sample to emit additional emission lights.

17. The optical system as defined in claim 16, wherein said excitation light delivery means and said at least one additional excitation light delivery means of said optical apparatus are located in said plane.

18. The optical system as defined in claim 16, wherein said excitation light delivery means and said at least one additional excitation light delivery means of said optical apparatus are diagonally aligned in said plane.

19. The optical system as defined in claim 12, wherein said optical apparatus further comprises a plug and probe assembly for holding said reflector and said collector and aligning said flow cell and said excitation light delivery means.

20. The optical system as defined in claim 12, wherein said emission light detection means further comprising at least one emission light filter.

21. The optical system as defined in claim 12, wherein said emission light detection means further comprising at least one photo-multiplier tube detector.

22. A method of improving collection efficiency in an optical instrument for optical detection utilizing a capillary flow cell to contain a sample, the method comprising the steps of:

a. positioning a concave reflector with an optical axis having a concave surface at one side of said flow cell for said concave surface to reflect emission lights emitted by the sample;
b. positioning a lens collector having a proximal convex surface and a distal convex surface at an opposite side of said flow cell for said proximal convex surface to collect said emission lights and for said distal convex surface to collimate said emission lights;
c. delivering an excitation light at a close proximity of said flow cell along a direction in a plane orthogonal to said optical axis to cause said sample to emit said emission lights; and
d. detecting said collimated emission lights.

23. The method as defined in claim 22, further comprising the step of forming said collector with a high refractive index ball lens.

24. The method as defined in claim 22, further comprising the step of forming said collector with a first lens having said proximal convex surface and a second lens having said distal convex surface.

25. The method as defined in claim 22, further comprising the step of delivering at least one additional excitation light at a close proximity of said flow cell to cause said sample to emit additional emission lights.

26. The method as defined in claim 25, further comprising the step of delivering said excitation light and said at least one additional excitation light along respective directions in said plane.

27. The method as defined in claim 25, further comprising the step of delivering said excitation light and said at least one additional excitation light along respective diagonal directions in said plane.

28. The method as defined in claim 21, further comprising the step of providing a plug and probe assembly for holding said reflector and said collector and aligning said flow cell and said excitation light delivery means.

29. The method as defined in claim 21, further comprising the step of filtering said collimated emission lights.

30. The method as defined in claim 21, further comprising the step of providing at least one photo-multiplier tube detector for detecting said collimated emission lights.

* * * * *